United States Patent [19]

Maeyama et al.

[11] Patent Number: 4,585,648
[45] Date of Patent: Apr. 29, 1986

[54] DENTIFRICE COMPOSITION COMPRISING ZIRCONIUM-BONDED SYNTHETIC AMORPHOUS SILICATE

[75] Inventors: Tsutomu Maeyama, Chiba; Kenji Kaneko; Shigeru Ishii, both of Tokyo, all of Japan

[73] Assignee: Lion Corporation, Tokyo, Japan

[21] Appl. No.: 638,679

[22] Filed: Aug. 8, 1984

[30] Foreign Application Priority Data

Aug. 24, 1983 [JP] Japan .................. 58-153156

[51] Int. Cl.$^4$ ............................ A61K 7/16; A61J 3/02
[52] U.S. Cl. .................................. 424/49; 51/308; 424/50; 514/558; 514/560; 424/14
[58] Field of Search .................... 51/308; 424/49, 309, 424/14

[56] References Cited

U.S. PATENT DOCUMENTS

| | | | |
|---|---|---|---|
| 3,257,282 | 6/1966 | Muhler | 424/52 |
| 3,330,732 | 7/1967 | Muhler | 424/14 |
| 3,378,445 | 4/1968 | Muhler | 424/49 |
| 3,450,813 | 6/1969 | Muhler | 424/52 |
| 3,541,017 | 11/1970 | Muhler | 424/49 X |
| 3,576,750 | 4/1971 | Muhler | 424/49 |
| 3,955,942 | 5/1976 | Cordon et al. | 424/49 |
| 4,089,943 | 5/1978 | Roberts et al. | 424/49 |
| 4,303,641 | 12/1981 | De Wolf et al. | 424/49 |
| 4,474,824 | 10/1984 | De Wolf et al. | 427/215 X |

FOREIGN PATENT DOCUMENTS

| | | | |
|---|---|---|---|
| 1348492 | 3/1974 | United Kingdom | 252/89.1 |
| 2057880 | 4/1981 | United Kingdom | 424/49 |

Primary Examiner—John E. Kittle
Assistant Examiner—Mukund J. Shah
Attorney, Agent, or Firm—Birch, Stewart, Kolasch & Birch

[57] ABSTRACT

A dentifrice composition having an excellent storage-stability which comprises a zirconium-bonded synthetic amorphous silicate (zirconosilicate) with a zirconium content of 0.1 to 10% by weight as $ZrO_2$ based on $SiO_2$ and a dentifrice vehicle containing water, humectant and flavor, and by adjusting the refractive index of the vehicle substantially identical with that of the silicate, the dentifrice composition can be made transparent.

23 Claims, 15 Drawing Figures

DENTIFRICE COMPOSITION COMPRISING ZIRCONIUM-BONDED SYNTHETIC AMORPHOUS SILICATE

BACKGROUND OF THE INVENTION

This invention relates to a dentifrice composition comprising, as an abrasive, a zirconium-bonded synthetic amorphous silicate (zirconosilicate) with a zirconium content of between 0.1 to 10% by weight as $ZrO_2$ based on $SiO_2$ and, more specifically, it relates to a dentifrice composition which is excellent in storage-stability and can be made transparent by adjusting the refractive index of the dentifrice vehicle substantially identical with that of the zirconium-bonded synthetic amorphous silicate.

As an abrasive for dentifrice compositions, calcium secondary phosphate, calcium carbonate, aluminum hydroxide, etc. have usually been used. Since it is important for the abrasive that is has excellent storage-stability as well as high cleaning performance for teeth and good taste, abrasives possessing improved storage-stability have been demanded.

Furthermore, as an abrasive for use in the preparation of transparent dentifrice compositions, amorphous anhydrous silicas obtained through the reaction of sulfuric acid and sodium silicate have been known, as well as those anhydrous silica abrasives as described in Japanese Patent Publication No. 11159/1974, Japanese patent Laid-Open No. 75742/1974, Japanese Patent Publication No. 14935/1973, etc. Although these known silica abrasives have some advantageous features which can be used for producing transparent dentifrices, the products obtained therefrom are poor in commercial values. In general, these amorphous anhydrous silica abrasives are inferior in storage stability, especially in respect of the refractive index. Therefore, it will be happen that the transparent toothpastes having the conventional silica abrasives blended therein are deteriorated in terms of transparency in the storage test. Furthermore, the conventional amorphous anhydrous silica abrasives can not be blended in a great amount because they generally have a large liquid absorption and it is difficult to prepare the amorphous anhydrous silica abrasives so as to reduce their absorption. In order to obtain a transparent dentifrice having a desired viscosity at a desired abrasing level by using the conventional silica abrasives, it is necessary to condition the composition of the transparent dentifrice vehicle. Therefore, conventional amorphous anhydrous silica abrasives involve a problem with respect to the blendability.

SUMMARY OF THE INVENTION

An object of the present invention is to provide a dentifrice composition which is excellent in storage stability.

Another object of the present invention is to provide a transparent dentifrice composition of which the transparency scarcely changes even after a long-term storage.

More specifically, as the result of a study on abrasives for use in dentifrice compositions which are excellent in storage-stability as well as have desired cleaning performance and taste, the inventors have found that a zirconium-bonded synthetic amorphous silicate (zirconosilicate) having a zirconium content of 0.1–10% by weight as $ZrO_2$ based on $SiO_2$ has a performance capable of effectively attaining the foregoing object as the dentifrice abrasive. Moreover, it has also been found that, in the case of using the zirconium-bonded synthetic amorphous silicate as the abrasive for use in a transparent dentifrice composition, the zirconium-bonded synthetic amorphous silicate shows less change in the refractive index even after a long-term storage, and hence maintains the transparency of the dentifrice composition even during a long-term storage or storage in cold or warm districts, resulting in providing a transparent dentifrice composition which is excellent in the stability of the transparency.

Therefore, this invention provides a dentifrice composition comprising as an abrasive a zirconium-bonded synthetic amorphous silicate (zirconosilicate) with a zirconium content of 0.1–10% by weight as $ZrO_2$ based on $SiO_2$, blended with a dentifrice vehicle containing water, humectant and flavour.

The dentifrice composition of the present invention which contains the zirconium-bonded synthetic amorphous silicate as an abrasive shows an excellent storage-stability, i.e. a good shape retention and less syneresis even after a long-term storage at a high temperature.

According to the present invention, a transparent dentifrice composition can be obtained by adjusting the refractive index of the dentifrice vehicle substantially identical with that of the zirconium-bonded synthetic amorphous silicate. The thus obtained transparent dentifrice composition may keep its transparency for a long time at various storage temperatures because the zirconium-bonded synthetic amorphous silicate shows less change in the refractive index and maintains the substantial identity of the refractive index with that of the vehicle even after a long-term storage.

Further, the zirconium-bonded synthetic amorphous silicate having a desired liquid absorption may be used singly or mixed with other abrasives to obtain a dentifrice composition which has an adequate viscosity and can be extruded with ease from a container.

The above and other objects, features, and advantages of the present invention will be more fully understood by reading the following description taken in conjunction with the accompanying drawings.

DETAILED DESCRIPTION OF THE INVENTION

Figure 1:
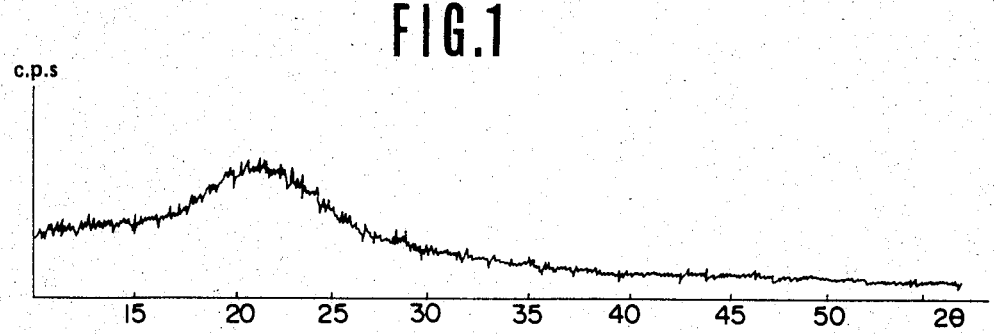
FIG. 1 is an X-ray diffraction chart for the heat treatment product of Zr-bonded silicate having 2.79% by weight of $ZrO_2$ content based on $SiO_2$.

In the dentifrice composition according to this invention, a zirconium-bonded synthetic amorphous silicate (zirconosilicate) is used as the abrasive.

The zirconium-bonded synthetic amorphous silicate used in this invention contains zirconium bonded with $SiO_2$ usually as the form of $ZrO_2$ and is different from mere mixtures of anhydrous silica with zirconium dioxide or zirconyl hydroxide, and crystalline zirconium silicate as shown in the Examples to be described latter.

It is preferred that the $SiO_2$ content in the zirconium-bonded synthetic amorphous silicate is more than 70% by weight and, particularly, more than 85% by weight of the anhydrous matter (zirconium-bonded synthetic amorphous silicate dried at 105° C. for 2 hours). The zirconium content in the zirconium-bonded synthetic amorphous silicate is in the range of 0.1 to 10% by weight, more preferably, 0.2–2% by weight as $ZrO_2$ based on $SiO_2$ in view of the liquid absorption, stability for transparency and abrasing power. If the zirconium content is less than 0.1% by weight as $ZrO_2$, no substantial advantage of using the zirconium-bonded synthetic amorphous silicate can be obtained. On the contrary, if the zirconium content is more than 10% by weight as $ZrO_2$, control for the physical properties thereof is difficult, which may be undesired as for the transparent dentifrice abrasive.

Further, the zirconium-bonded synthetic amorphous silicate may contain aluminum, magnesium, sodium, potassium, lithium, hafnium, etc. dispersed or bonded therein, which may possibly be introduced as impurities from sodium silicate, zirconyl chloride, sulfuric acid or the like as the starting material for the zirconium-bonded synthetic amorphous silicate. It is preferred that the content of the impurities is less than 10% by weight of the silicate.

Further, the amount of adsorbed water to the zirconium-bonded synthetic amorphous silicate may be less than 20% at 25° C. and 70% RH.

It is preferred that the zirconium-bonded synthetic amorphous silicate for use in this invention has a refractive index of 1.40 to 1.47, a specific surface area of less than 800 $m^2/g$, a specific gravity of 1.9 to 2.3 and a liquid absorption of 0.4 to 2.0 ml/g as measured by the methods shown in the Examples to be described later.

Furthermore, the zirconium-bonded synthetic amorphous silicate to be used as the abrasive preferably has an average particle size of less than 0.5 $\mu m$ when measured by the SEM method and an average particle size of 1–30 $\mu m$, particularly 2–20 $\mu m$ when measured by the sedimentation method.

The amount of the zirconium-bonded synthetic amorphous silicate blended into a dentifrice composition may preferably be in the range of 1 to 50% by weight and, more preferably, 5 to 30% by weight based on the total weight of the consumption.

The zirconium-bonded synthetic amorphous silicate as described above can be obtained, for instance, through a reaction of a mineral acid containing a zirconium salt with an alkali metal salt of silicic acid. The alkali metal salt of silicic acid may include sodium, potassium and lithium silicates, sodium silicate being preferred in view of its relatively inexpensive cost. The alkali metal salt of silicic acid may preferably have a molar ratio ($SiO_2/X_2O$, where X represent alkali metal) between 2 to 4. The mineral acid for acidifying the alkali metal silicate includes, for instance, hydrochloric acid, sulfuric acid and nitric acid.

In the case of preparing the zirconium-bonded synthetic amorphous silicate through the reaction of alkali metal silicate and mineral acid, it is necessary to add a zirconium salt. The zirconium salt usuable herein includes preferably water-soluble zirconium salt, for example, zirconyl chloride ($ZrOCL_2$), zirconyl sulfate, sirconyl acetate, etc. In this case, it is most suitable to previously add a zirconium salt to mineral acid, and then react the alkali metal silicate therewith.

The foregoing step is very effective because zirconium-bonded synthetic amorphous silicates of various levels of abrasing power and liquid absorption can be produced depending on the zirconium content and, accordingly, the abrasing power and the liquid absorption can be adjusted with ease.

In the preparation of the dentifrice composition according to this invention, the zirconium-bonded synthetic amorphous silicate is kneaded with a dentifrice vehicle. The dentifrice vehicle comprises water, humectant and flavors as essential ingredients. In this case, a transparent dentifrice composition can be obtained by making the vehicle transparent and adjusting the refractive index thereof substantially equal to that of the zirconium-bonded synthetic amorphous silicate.

The humectant usable herein includes one or more of glycerine, sorbitol, polyethylene glycol of an average molecular weight of 200 to 6000, ethylene glycol, propylene glycol, reducing starch sugar, xylytol, etc. which may be blended in an amount of 10 to 80%, preferably 30 to 60% by weight based on the total weight of the composition.

The vehicle contains one or more flavors including essential oils such as peppermint and spearmint, flavor materials such as l-menthol, carvone, eugenol, anethole, etc. The blending amount thereof is usually 0.1 to 5%, preferably 0.5 to 2% by weight of the composition.

Furthermore, a sweetening agent such as sodium saccharin, asparzyme, stevioside, neohesperidyl-dihydrochalcone, glycyrrhizin, perillartine, p-methoxycinnamic aldehyde, etc. may be blended singly or in combination with the blending amount usually between 0 to 5%, preferably 0.01 to 5%, more preferably 0.05 to 2% by weight of the composition.

The vehicle may be incorporated as desired with one or more of binders which include carrageenan, sea weed extracts, cellulose derivatives such as sodium carboxymethylcellulose, alkali metal ailgnates such as sodium alginate, gums such as xanthane gum, synthetic binders such as polyvinyl alcohol, carboxyvinyl polymers (e.g., Carbopol (registered trade mark)), and polyvinyl pyrrolidone, inorganic binders such as gelling amorphous anhydrous silica, Veegum (registered trade mark), kaolin, bentonite, etc. The binder may be blended in an amount of 0 to 5% and, particularly 0.1 to 5% by weight of the total weight of the dentifrice composition. Among them, sodium carboxymethylcellulose and carboxyvinyl polymers are particularly preferred.

Furthermore, the dentifrice vehicle may be blended as required with one or more of surfactants including anionic surfactants such as water soluble salts of higher alkyl sulfates having 8 to 18 carbon atoms in the alkyl group (for example, sodium lauryl sulfate and sodium myristal sulfate), $\alpha$-olefin sulfonates (for example, sodium $\alpha$-olefin sulfonate having 14 carbon atoms), 2-hydroxy alkane sulfonates, water soluble salts of higher fatty acid monoglyceride sulfonates having 10 to 18 carbon atoms in the fatty acid group (for example, sodium lauryl monoglyceride sulfonate and sodium coconuts monoglyceride sulfonate), higher fatty acid sodium monoglyceride monosulfates, salts of amides of higher fatty acid having 12 to 18 carbon atoms in the fatty acid group with lower aliphatic amino acids (for example, sodium-N-methyl-N-plamitoyl tauride, sodium-N-lauroyl-sarcosinate, sodium-N-lauroyl-$\beta$-alanine, sodium-N-long chain acyl amino acids, etc.), as well as nonionic surfactants such as alkloyl diethanol amides having 10 to 16 carbon atoms in the fatty acid group, stearyl monoglyceride, sucrose fatty acid esters having 12 to 18 carbon atoms in the fatty acid group (for example, sucrose mono- and di-laurate), lactose fatty acid esters, lactitol fatty acid esters, maltitol fatty acid esters, polyoxyethylene (60 moles) sorbitan monostearate, polymers of ethylene oxide and propylene oxide and derivatives thereof (for example, polyoxyethylene polyoxypropylene monolauryl ester), etc. The blending amount of the surfactant is usually 0 to 5%, preferably 0.1 to 5%, more preferably 0.5 to 2%.

There may be further added preservatives such as sodium dihydroacetate, p-hydroxymethyl benzoic acid, p-hydroxyethyl benzoic acid, p-hydroxybutyl benzoic acid and sodium benzoate, etc., microcrystalline cellulose powders such as Avicel (Trade Mark), gelatine, and the other ingredients. The dentifrice vehicle may also contain one or more effective ingredients which include enzymes such as dextranase, amylase, protease, mutanase, phosphatase, lysozyme and lytic enzyme, alkali metal monofluorophosphate such as sodium monofluorophosphate and potassium monofluorophosphate, fluorine compounds such as sodium fluoride and stannous fluoride, stannous compounds such as stannous pyrophosphate, chlorhexydine salts such as chlorhexydine hydrochloride and chlorhexydine gluconate, sodium copper chlorophyllin, hinokitiol, $\epsilon$-aminocaproic acid, tranexamic acid, ethane dihydroxydiphosphonate, allantoin chlorohydroxy aluminum, dihydrocholesterol, glycyrrhizin, glycyrrhizinic acid, azulene, crude drugs such as chamomile, chlorophyl, chelating phosphoric acid compounds such as glycelophosphate, sodium chloride and water soluble inorganic phosphoric acid compounds in an effective amount.

Futhermore, in addition to the zirconium-bonded synthetic amorphous silicate, other abrasives and polishing agents including amorphous anhydrous silica, aluminosilicate, calcium secondary phosphate dihydrate, calcium secondary phosphate anhydrate, calcium carbonate, insoluble sodium metaphosphate, aluminum hydroxide, alumina, polymethyl methacrylate, crystalline zirconium silicate, titanium dioxide, etc. may be blended into the composition. In the case of preparing a transparent dentifrice composition by using the zirconium-bonded synthetic amorphous silicate, the abrasives ordinarily used for transparent dentifrices such as amorphous anhydrous silica and aluminosilicate, and the abrasives and the polishing agents tending to decrease the transparency of the transparence dentifrice composition may also be blended. However, the abrasive and the polishing agent tending reduce the transparency are blended by the amount preferably less than 10% by weight of the total weight of the composition and, more preferably, less than 10% by weight of the zirconium-bonded synthetic amorphous silicate. Further, the zirconium-bonded synthetic amorphous silicate having a desired liquid absorption may be mixed with the above-described abrasive to obtain an opaque toothpaste composition that has an adequate viscosity and can be extruded with ease from a tubular container.

The following examples will further illustrate the practice of the present invention particularly when taken in conjunction with comparative examples. They are given by way of illustration and are not to be construed as limiting the invention.

[EXAMPLE 1]

Zirconium-bonded synthetic amorphous silicates having various zirconium contents were prepared by the process described below.

Preparation Of Zirconium-Bonded Synthetic Amorphous Silicate to a 20 liter volume reactor with buffle plates provided with a stirrer having a turbine blade of 150 mm diameter, were charged 10 kg of an aqueous solution of sodium silicate ($Na_2O \cdot 3.1SiO_2$) containing 100 g/kg of $SiO_2$ and 20 g/kg of NaCl, and 3688 g of 10% sulfuric acid cotaining zirconyl chloride at various concentrations were added at the flow rate of 36 g/min while maintaining the reaction temperature at 87° C. Then, 10% sulfuric acid was added at a flow rate of 83 g/min and, when the pH value of the reaction system reached 2.8, the addition of the acid was stopped and the reaction product was aged for 15 min as it was. Thereafter, filtration and water washing were repeated and after drying in a drier kept at 110° C., the product was finely pulverized to obtain zirconium-bonded synthetic amorphous silicate (hereinafter referred to as Zr-bonded silicate) containing various zirconium contents.

As the comparison, amorphous anhydrous silica containing no zirconium synthesized in the foregoing reaction step without adding zirconyl chloride (hereinafter referred to as amorphous anhydrous silica) and mixtures prepared by mixing zirconyl hydroxide ($ZrO(OH)_2$) obtained by the foregoing process using an aqueous solution of sodium hydroxide containing 33 g/kg of $Na_2O$ and 20 g/kg of NaCl instead of the aqueous sodium silicate solution with the amorphous anhydrous silica in various ratios (hereinafter referred to as mixture) were also produced.

Then, the Zr-bonded silicates and the mixtures produced as above were examined for their X-ray diffraction, refractive index, minimum turbidity, liquid absorption, acid solubility, ignition loss, specific surface area and specific gravity, respectively.

I X-Ray Diffraction

The samples were heat treated at 900° C. for one hour and X-ray diffraction of the samples were measured by using a Geigerflex RAD-IA model maufactured by Rigaku Denki Co. as the X-ray diffraction apparatus (4 KV, 30 mA, CuKα-ray, Ni filter).

Figure 2:
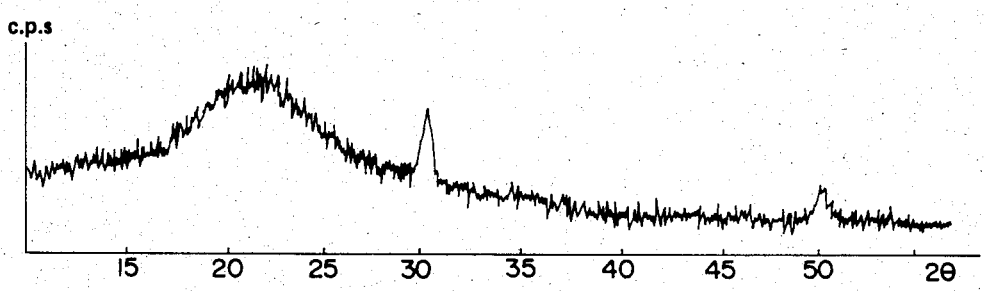
FIG. 2 is an X-ray diffraction chart for the heat treatment product of a mixtures of anhydrous silica and zirconyl hydroxide.
Figure 3:
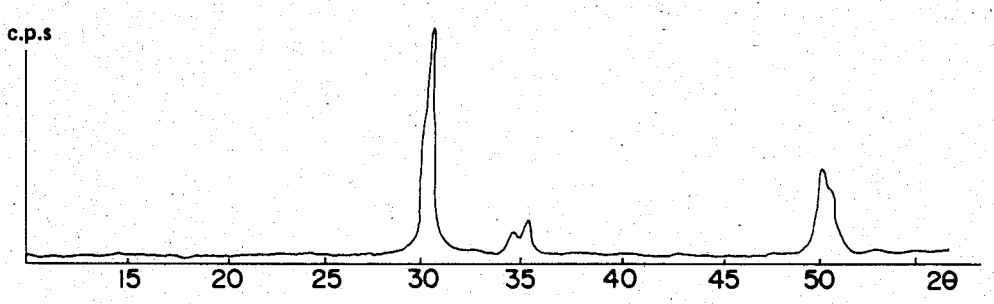
FIG. 3 is an X-ray diffraction chart for the heat treating product of zirconyl hydroxide.
Figure 4:
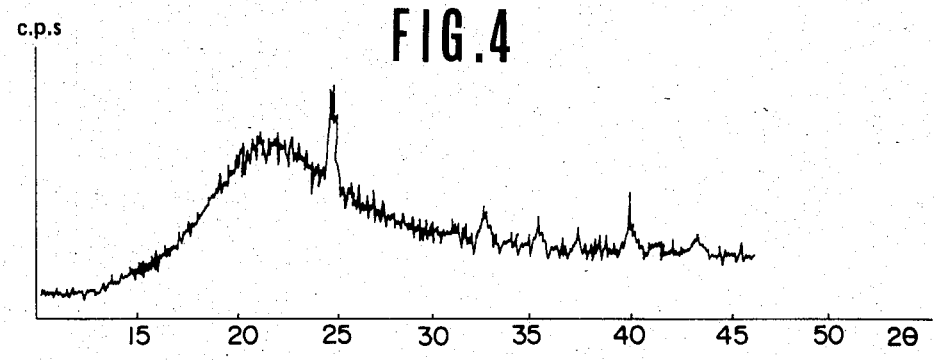
FIG. 4 is an X-ray diffraction chart for a mixture of anhydrous silica and zircon flower.
Figure 5:
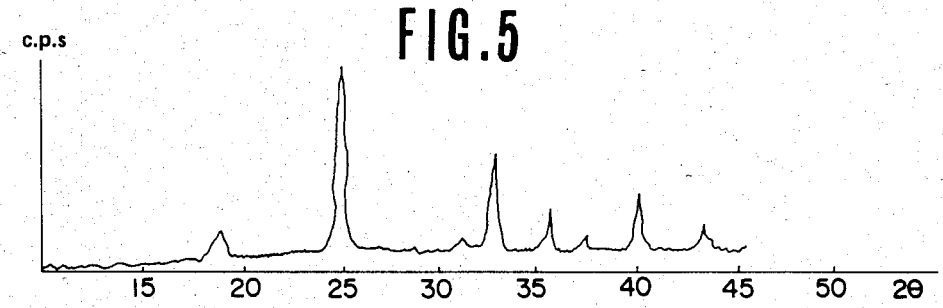
FIG. 5 is an X-ray diffraction chart for zircon flower.
Figure 6:
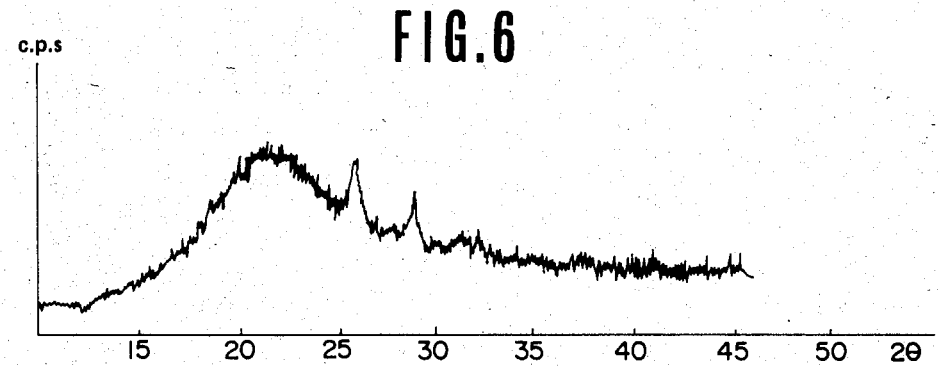
FIG. 6 is an X-ray diffraction chart for a mixture of anhydrous silica and monoclinic zirconium oxide.
Figure 7:
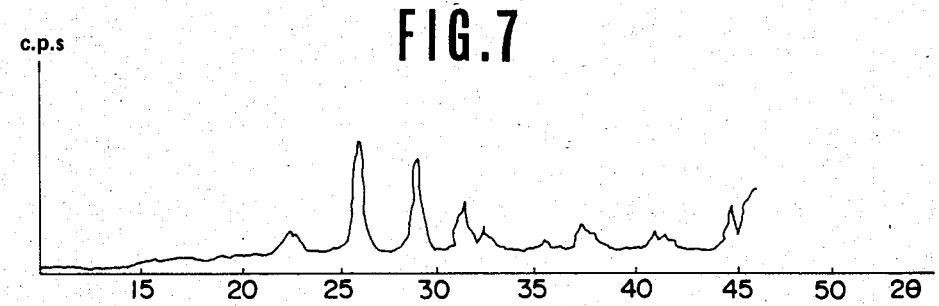
FIG. 7 is an X-ray diffraction chart for a monoclinic zirconium oxide.

FIG. 1 is a X-ray diffraction chart for the heat tgreatment product of Zr-bonded silicate having 2.79% by weight of $ZrO_2$ content based on $SiO_2$, FIG. 2 is a X-ray diffraction chart for the heat treatment product of a mixture of the anhydrous silica and zirconyl hydroxide (containing 2.80% by weight of zirconium as $ZrO_2$), FIG. 3 is a X-ray diffraction chart for the heat treatment product of zirconyl hydroxide, FIG. 4 is a X-ray diffraction chart for a mixture of the anhydrous silica and zircon flower (crystalline zirconium silicate) (containing 3% by weight of zirconium as $ZrO_2$), FIG. 5 is a X-ray diffraction chart for zircon flower, FIG. 6 is a X-ray diffraction chart for a mixture of the anhydrous silica and monoclinic zirconium oxide (containing 3% by weight of zirconium as $ZrO_2$) and FIG. 7 is a X-ray diffraction chart for monoclinic zirconium oxide.

As apparent from the above results, the mixtures or anhydrous silica and zirconyl hydroxide show similar diffraction peaks to those of tetragonal zirconium oxide obtained through the heat treatment of zirconyl hydroxide, and the mixtures of anhydrous silicas and other crystalline zirconium compounds show similar diffraction peaks to those of the starting crystalline zirconium compounds to which the silicas were mixed. While on the other hand, the Zr-bonded silicates do not show the similar diffraction peaks to those of the mixtures at all even after the heat treatment but were in the amorphous state showing that zirconium is uniformly bonded and present in the amorphous silicate.

II Refractive Index And Turbidity

The refractive index and the turbidity were measured by the following methods for the Zr-bonded silicates having various zirconium contents and the anhydrous silica-zirconyl hydroxide mixtures containing corresponding amounts of zirconium, respectively.

Figure 8:
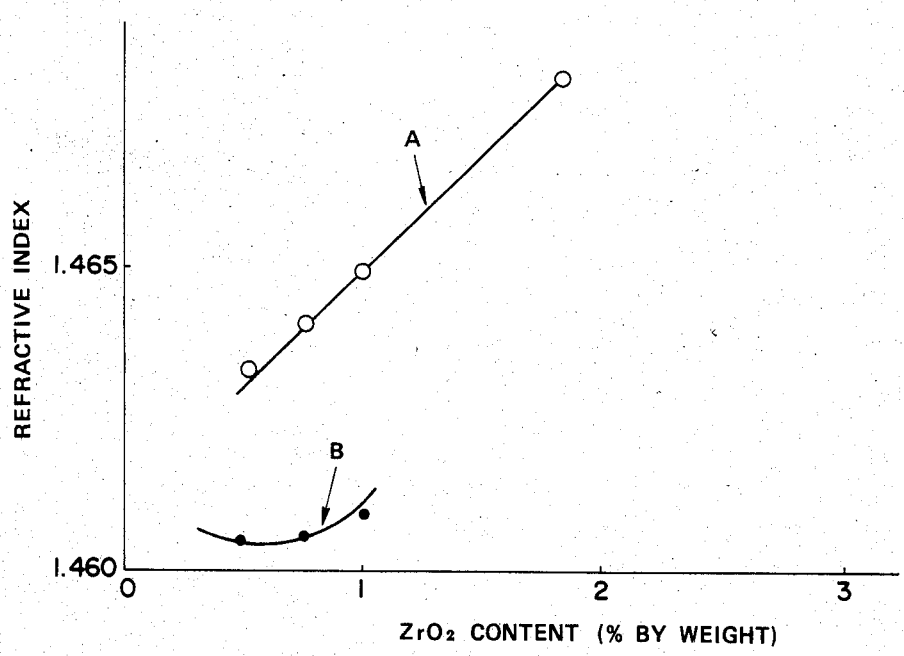
FIG. 8 is a graph showing the refractive index for Zr-bonded silicates and mixtures of anhydrous silica and zirconyl hydroxide.
Figure 9:
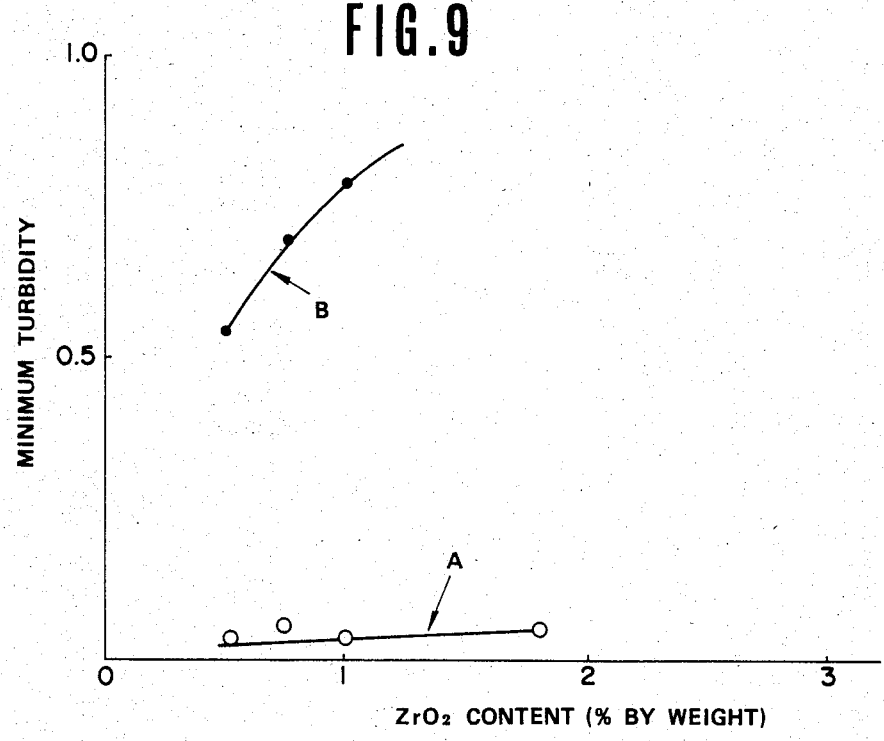
FIG. 9 is a graph showing the minimum turbidity of Zr-bonded silicates and mixture of anhydrous silica and zirconyl hydroxide.

FIG. 8 shows the refractive index and FIG. 9 shows the turbidity. In the figures, "A" represents the Zr-bonded silicates and "B" represents the mixtures.

Measurement Of Refractive Index And Turbidity

Glycerin and water were mixed properly to prepare dispersants having various refractive indexes. 15 g of the sample were dispersed into each 35 g of the dispersants and mixed under defoaming in a vacuum stirring crusher for 10 min.

the refractive index and the turbidity for each of the dispersions at 25° C. were measured, and refractive index-turbidity curves were drawn to determine the refractive index of the dispersion at as the minimum turbidity as the refractive index of the sample.

In this experiment, Abbe's refractometer was used for the measurement of the refractive index and an integrating sphere type turbid meter was used for the measurement of the turbidity. The turbidity was determined based on the transparency at 1 mm thickness of the specimen.

As can be seen from the results shown in FIG. 8 and FIG. 9, it was observed that in the case of a mixture merely incorporating zirconyl hydroxide to the anhydrous silica, the zirconyl hydroxide behaved as a masking agent so that the minimum turbidity increased as the amount of the zirconyl hydroxide increased to make the dispersion turbid but with scarce fluctuation in the refractive index. On the other hand, in the case of the Zr-bonded silicate, although the refractive index changed depending on the zirconium content, the turbidity scarcely varied. Accordingly, it was recognized that the Zr-bonded silicate is not a mere mixture of zirconyl hydroxide but zirconium is uniformly bonded in the anhydrous silicate.

III Liquid Absorption

Figure 10:
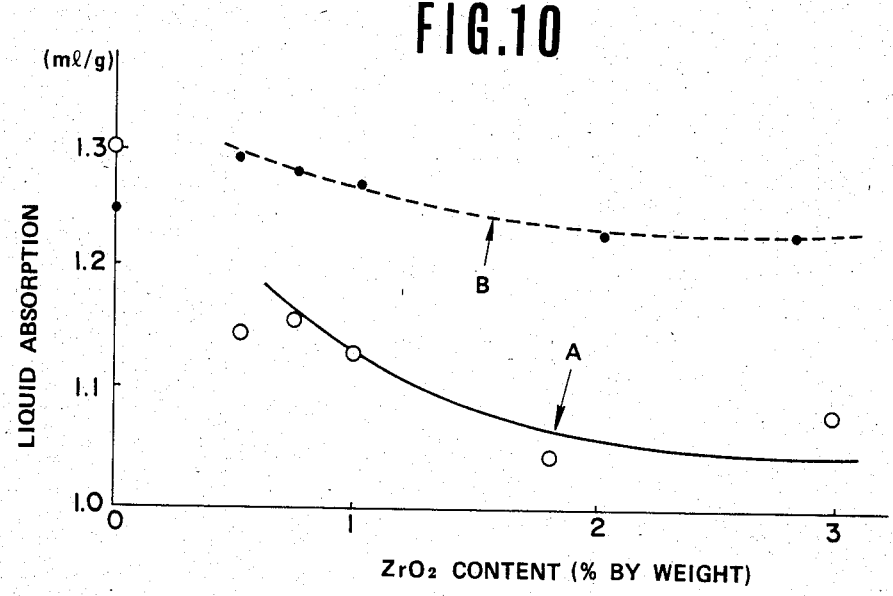
FIG. 10 is a graph showing the liquid absorption of the Zr-bonded silicates and mixtures of anhydrous silica and zirconyl hydroxide.

The liquid absorption was measured by the following method for the Zr-bonded silicates having various zirconium contents and for the anhydrous silica-zirconyl hydroxide mixtures containing corresponding amounts of zirconium, to obtain the results as shown in FIG. 10.

Measurement Of Liquid Absorption

Anhydrous product obtained from a sample by drying 105° C. for 2 hours to remove adsorbed water was weighed by 1.0 g, which was placed on a glass plate and uniformly mixed with 5 ml of aqueous solution of 42.5% glycerin. The glycerin solution was added little by little through a microburet to the sample and the mixing of the sample and the glycerin solution was carried out so that the sample was infiltrated entirely with the glycerin solution by using a stainless steel spatula. The end point was determined when the sample became granular and further gathered into a hard plaster-like mass but the mixture of the sample and glycerin did not stick to the glass plate. The amount of the liquid required (ml) was determined as the liquid absorption.

As can be seen from the results shown in FIG. 10, an apparent difference is observed for the liquid absorption betgween the mixture in which the zirconyl hydroxide is merely mixed to the amorphous silica and the Zr-bonded silicate, showing that the Zr-bonded silicate is different from the mixture.

Further, FIG. 10 also shows that the liquid absorption of the Zr-bonded silicate decreases as the zirconium content increases, which suggests that an abrasive having an optional absorption can be prepared with ease by adjusting the zirconium content in the Zr-bonded silicate, to provide great merit in preparing a dentifrice. On the other hand, in usual amorphous anhydrous silicas not bonded with zirconium, different from the Zr-bonded silicate, it is impossible to adjust the liquid absorption unless the production method is changed and, moreover, it is difficult to optionally produce anhydrous silicas having desired liquid absorption. In order to obtain a desired viscosity in a usual dentifrice based on amorphous anhydrous silica, it can not but change the composition of the dispersant (dentifrice vehicle). On the contrary, in the case of the Zr-bonded silicate, the abrasive with a desired absorption can be produced optionally by varying the zirconium content and, accordingly, a dentifrice having a desired viscosity can be prepared with ease by using a Zr-bonded silicate having a desired absorption, which means that the Zr-bonded silicate has an excellent blendability.

IV Acid Solubility

The acid solubility (zirconium leaching rate) was examined by the following method for the Zr-bonded silicates of various zirconium contents and for the anhydrous silica-zirconyl hydroxide mixtures containing corresponding amounts of zirconium. The results are shown in Table 1.

Measurement Of Zirconium Leaching Rate 2 g of sample were placed into a 300 ml volume tall beaker, to which 100 ml of 2N HCl was added and boiled for one hour. After cooling, the solution was filtered by using No. 5C filter paper and the filtrate was transferred to a 250 ml volume measuring flask and used as a test solution.

Then, the zirconium amount in the test solution was measured by the colorimetry according to Arsenazo III to determine the zirconium leaching amount (a g) per 100 g of the sample.

On the other hand, 100 g of the sample was placed on a platinum dish, to which was added 10 ml of water, 0.5 ml of 50% sulfuric acid and 10 ml of hydrofluoric acid. After evaporating to dry on a sand bath, the zirconium content per 100 g of the sample (b g) was determined in the same manner as described above, and the zirconium leaching rate was calculated by the following equation:

Zirconium leaching rate $(\%) = a/b \times 100$

TABLE 1

| ZrO$_2$ content (b g) | Zirconium leaching rate (%) | |
|---|---|---|
| 0.50 | 10.4 | The Invention (Zr-bonded silicate) |
| 1.5 | 15.8 | The Invention (Zr-bonded silicate) |
| 2.0 | 25.6 | The Invention (Zr-bonded silicate) |
| 0.50 | 79.1 | Comparison (mixture) |
| 1.5 | 80.5 | " |
| 2.0 | 81.0 | " |

From the results shown in Table 1, it is recognized that the Zr-bonded silicates, different from the anhydrous silica-zirconyl hydroxide mixtures, show extremely less zirconium leaching in hydrochloric acid and that the Zr-bonded silicates contain zirconium bonded in the anhydrous silicate.

V Ignition Loss

Figure 11:
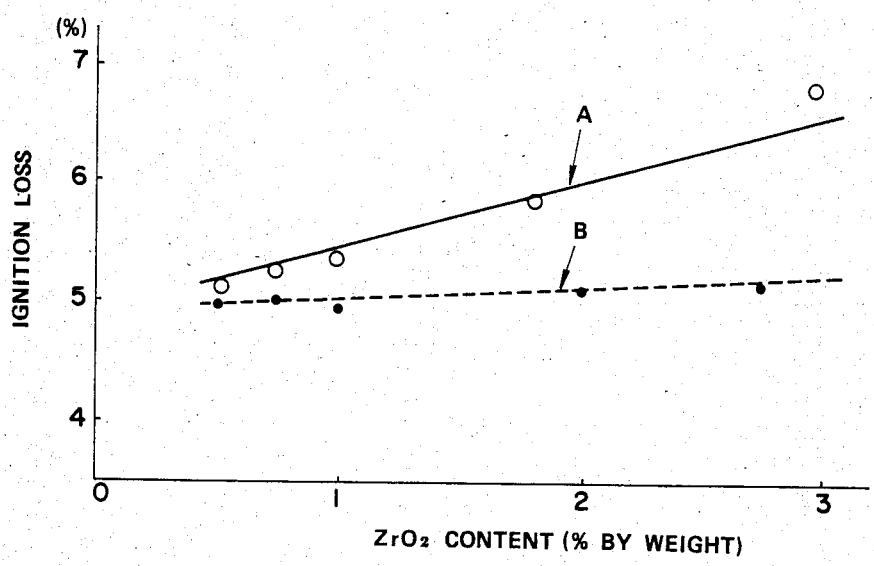
FIG. 11 is a graph showing the ignition loss of Zr-bonded silicates and mixtures of anhydrous silica and zirconyl hydroxide.

The ignition loss was measured by the following method for the Zr-bonded silicates having various zirconium contents and the anhydrous silica-zirconyl hydroxide mixtures containing corresponding amounts of zirconium. The results are shown in FIG. 11.

Measurement For Ignition Loss 2 g of the sample was placed into a platinum crucible and the sample weight $W_1$ after drying at 105° C. for two hours was measured.

Then, the sample was heated intensely in an electric furnace at 900° C. for one hour and then allowed to cool in a desiccator. The sample weight $W_2$ was measured and the ignition loss is determined by the following equation:

$$\text{Ignition loss }(\%) = \frac{W_1 - W_2}{W_1} \times 100$$

As the results shown in FIG. 11, it is recognized that while the mixtures of the anhydrous silica and zirconyl hydroxide show ignition loss of about the addition average between them, the Zr-bonded silicates show greater loss, which means that zirconium is bonded in the anhydrous silicate.

VI Specific Surface Area

Figure 12:
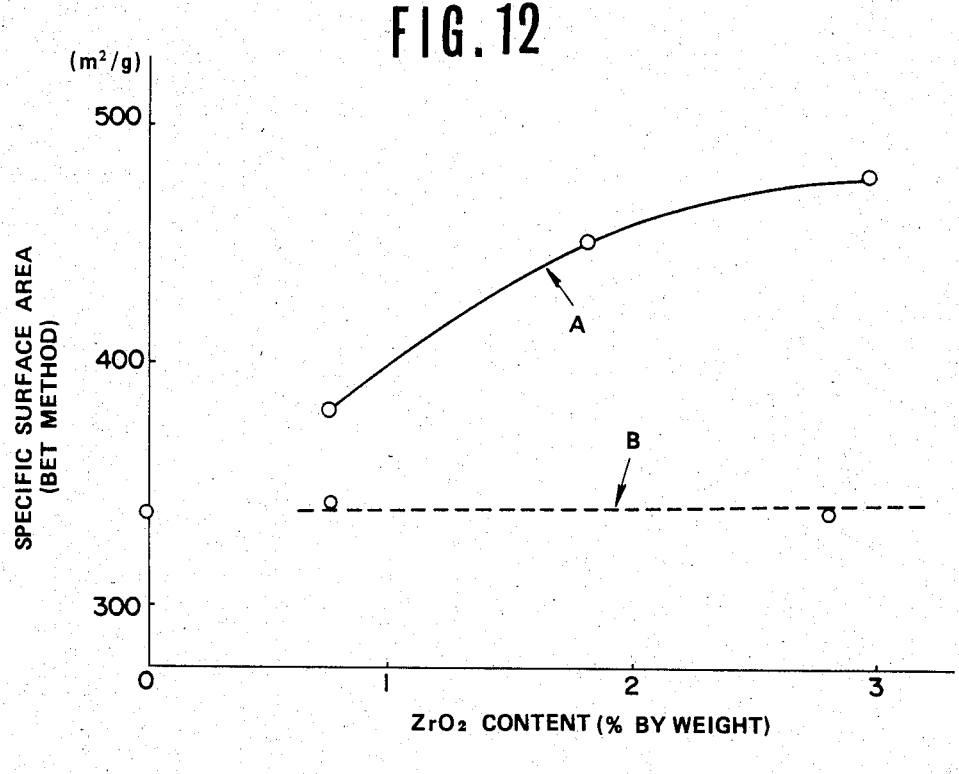
FIG. 12 is a graph showing the specific surface area of Zr-bonded silicates and mixtures of anhydrous silica and zirconyl hydroxide according to the BET method.

The specific surface area was measured by the BET method for the Zr-bonded silicates having various zirconium contents and the anhydrous silica-zirconyl hydroxide mixtures containing corresponding amounts of zirconium. The results are shown in FIG. 12.

Measurement For Specific Surface Area (BET Method)

Using liquid nitrogen as a coolant, the surface area per gram of the anhydrous matter was calculated by the BET method based on the nitrogen gas adsorption at −196° C. and assuming the molecular cross sectional area as 16.2 A$^2$.

In this case, the sample was degassed under $1 \times 10^{-5}$ mmHg of vacuum degree, at 140° C. for 60 min.

As can be seen from the result shown in FIG. 12, while the specific surface area scarcely changed in the mixtures of anhydrous silica and zirconyl hydroxide, increase in the specific surface area approximately proportional to the zirconium content was observed in the case of the Zr-bonded silicates. Accordingly, this also shows that zirconium is bonded in the anhydrous silicate in the case of the Zr-bonded silicates.

Typical properties of the Zr-bonded silicates and the anhydrous silica, and the anhydrous silica-zirconyl hydroxide mixture are shown in Table 2.

TABLE 2

| No. | ZrO$_2$ content (%) | Liquid absorption (ml/g) | Refractive index | Minimum turbidity | Ignition loss (%) | Zirconium leaching rate (%) | Specific surface area (m$^2$/g) BET method | Abrasion loss (mg) | Specific gravity | |
|---|---|---|---|---|---|---|---|---|---|---|
| 1 | 0.50 | 0.93 | 1.464 | 0.04 | 5.3 | 10.4 | 382 | 13.1 | 2.142 | The invention |
| 2 | 2.0 | 0.81 | 1.468 | 0.05 | 5.8 | 25.6 | 453 | 7.4 | 2.188 | (Zr-bonded silicate) |
| 3 | 0 | 1.06 | 1.461 | 0.03 | 4.7 | 0 | 325 | 19.8 | 2.128 | Anhydrous silica |
| 4 | 0.07 | 1.05 | 1.461 | 0.18 | 4.7 | 80.2 | 316 | 20.3 | 2.129 | |
| 5 | 0.50 | 1.05 | 1.461 | 0.55 | 4.8 | 79.1 | 342 | 19.5 | 2.135 | Mixture |
| 6 | 2.0 | 1.03 | 1.461 | 0.96 | 4.9 | 81.0 | 332 | 20.7 | 2.152 | |

Values for the abrasion loss and the specific gravity were determined by the following methods.

Abrasion Loss

An aqueous 60% glycerin solution containing 25% sample was placed on a smooth surface brass plate and abraded for 18000 cycles under a load of 500 g by using a horizontal reciprocal brushing type abrader. Then, the loss of the weight in the brass plate was measured, which was determined as the abrasion loss.

Measurement For Specific Gravity (1) Calibration for the specific gravity bottle (1) After cleaning and drying (105° C.) a 25 ml-volume specific gravity bottle, its weight ($W_P$) was measured.

(2) The specific gravity bottle was filled with boiled and cooled distilled water, left as it was in a balance chamber, applied with a cap and weighed accurately to 0.1 mg order ($W_L$).

(3) Just after the weighing, a thermometer was inserted into the specific gravity bottle to measure the water temperature ($T_a$).

The volume ($V_4$) of the specific gravity bottle at 4° C. was determined by the following equation:

$$V_4 \text{ (ml)} = \frac{(W_L - W_P) \cdot \delta_a}{1 + \alpha(T_a - 4)}$$

where $\delta_a$: specific volume of water at $T_a$°C.

$\alpha$: volume expansion coefficient of glass (0.000033)

(2) Measurement of the specific gravity (1) About 1.0 g of the sample (moisture content ($m_f$%) was measured separately) was charged in a specific gravity bottle and its weight ($W_S$) was measured.

(2) Distilled water was added to a depth of about 0.5 cm from the surface of the sample and placed under reduced pressure and normal pressure several times under vacuum. Then, the bottle was left in a balance chamber while filled with distilled water, and applied with a cap after the water was clarified. Then, the weight ($W_{S+L}$) and the temperature ($T_b$) were measured.

The specific gravity was measured by the following equations:

Dry weight ($W$) of the sample: $W \text{ (g)} = \dfrac{W_S - W_P}{1 + 0.01 \times m_f(\%)}$ The volume ($V_b$) of the specific gravity bottle at $T_b$°C.:

$$V_b(\text{ml}) = V_4\{1 + \alpha(T_b - 4)\}$$

The specific gravity (S) of the sample:

$$S = \frac{W}{V_b - (W_{S+L} - W_P - W) \cdot \delta_b}$$

(where $\delta_b$: specific volume of water at $T_b$°C.)

[EXAMPLE 2]

Toothpastes having the following formulation were prepared using Zr-bonded silicate having $ZrO_2$ content of 0.5% by weight based on $SiO_2$ and amorphous anhydrous silica (Zeodent 113 ®), respectively, and they were filled in aluminum-laminated plastic tubes to measure the storage-stability (retention and syneresis). The results are shown in Table 3.

| Toothpaste formulation | % |
|---|---|
| Abrasive | 25.0 |

-continued

| Toothpaste formulation | % |
|---|---|
| 96% Glycerin | 10.0 |
| 70% Sorbitol | 32.0 |
| Propylene glycol | 4.0 |
| Sodium carboxymethylcellulose | 1.2 |
| Sodium lauryl sulfate | 1.5 |
| Sodium saccharine | 0.1 |
| Flavor | 1.0 |
| Purified water | balance |
| Total | 100.0% |

TABLE 3

| | | | Storage condition | | | | | |
|---|---|---|---|---|---|---|---|---|
| | | Immediately after preparation | One month | | | Three month | | |
| Abrasive | Item | | Room temperature | 40° | 50° | Room temperature | 40° | 50° |
| The invention (Zr-bonded silicate) | Shape retention | 3 | 3 | 3 | 3 | 3 | 3 | 3 |
| | Syneresis | 1 | 1 | 1 | 2 | 1 | 2 | 3 |
| Amorphous anhydrous silica | Shape retention | 3 | 3 | 3 | 2 | 2.5 | 3 | 3.5 |
| | Syneresis | 1 | 1 | 2 | 3 | 2 | 3 | 4 |

From the above results, it is recognized that the toothpaste blended with the Zr-bonded silicate as an abrasive according to this invention has an excellent shape retention and results in less syneresis, and hence is excellent in the storage-stability.

The method of evaluation and the standards thereof for the shape retention and syneresis are as follows.

SHAPE RETENTION

Method of evaluation

The outer shape of the toothpaste when extruded out of a tube was estimated based on the visual observation according to the following estimation standards.

ESTIMATION STANDARDS

Score

Figure 13:
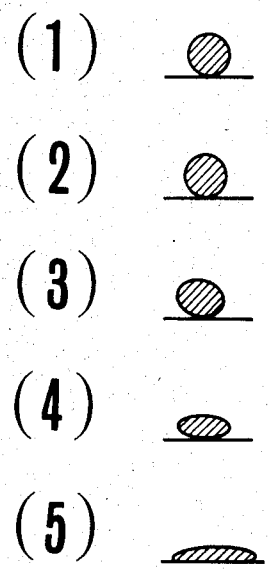
FIGS. 13(1)–(5) are cross sectional views showing the state of toothpaste compositions upon extrusion from a tube in the case of estimating the shape retention of toothpaste compositions.

5: As shown in FIG. 13(1), extruded toothpaste keeps the circular shape at the exit of the tube as it is and the mass of paste tends to tumble instably and falls out of a toothbrush.

4: As shown in FIG. 13(2), extruded toothpaste retains the circular shape of the tube exit at its upper portion while slightly flattens at the bottom.

3: As shown in FIG. 13(3), extruded toothpaste is in a preferred state for use almost keeping the shape of the tube exit and flattened at the bottom, thus placed stably on a toothbrush.

2: As shown in FIG. 13(4), extruded toothpaste is soft and loses lost the circular shape but does not flow into the planted fibers of a toothbrush.

1: As shown in FIG. 13(5), extrded toothpaste flows into the planted fibers of a toothbrush.

SYNERESIS

Method of evaluation

The extent of separation of liquid phase in the toothpaste upon extrusion from the tube was estimated by visual observation according to the following standards.

ESTIMATION STANDARDS

Score
1: No liquid separation is recognized at all.
2: Slight liquid separation is observed at the exit of the tube.
3: Liquid separation is observed at the exit of the tube, but with no practical problem.
4: Remarkable liquid separation is observed at the exit of the tube and liquid separation occurs in a viscous appearance throughout the entire portion.
5: Distinct liquid separation is observed throughout the entire portion.
6: Out of the standards.

[EXAMPLE 3]

Toothpastes having the formulations shown in Table 4 and Table 5 were prepared using the Zr-bonded silicate having a $ZrO_2$ content of 0.3% by weight based on $SiO_2$ and the amorphous anhydrous silica as the abrasive, respectively, and adjusting their refractive indexes variously. After storing the toothpastes at a predetermined temperature for one month, the turbidity at each of the refractive indexes was measured in the same manner as in Example 1.

Figure 14:
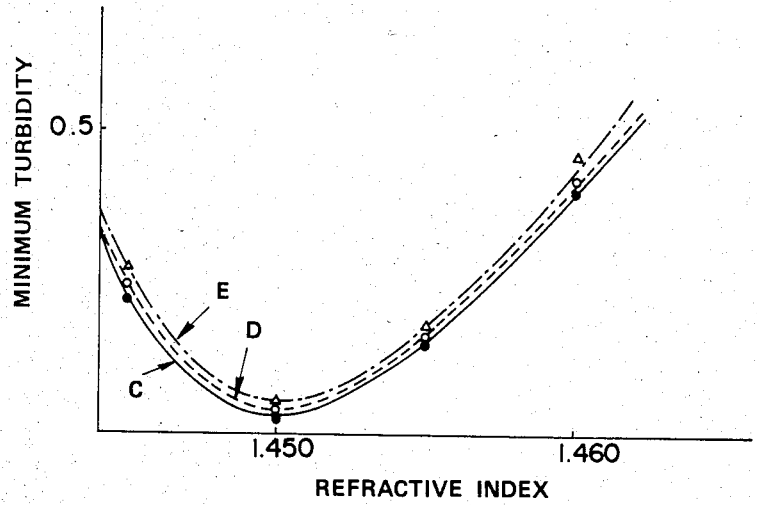
FIG. 14 is a graph showing the change in the transparency at various refractive indexes in the case where toothpaste compositions using Zr-bonded silicates as the abrasive are stored under various conditions.
Figure 15:
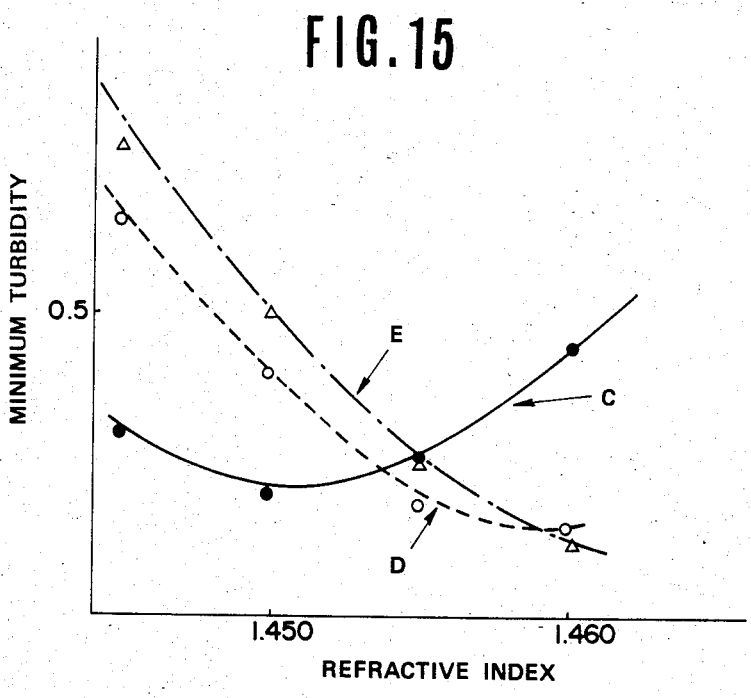
FIG. 15 is a graph showing the change in the transparency at various refractive indexes in the case where toothpaste compositions using amorphous anhydrous silica as the abrasive are stored under various conditions.

FIG. 14 shows the result of the measurement for the turbidity of the toothpastes containing the Zr-bonded silicate and FIG. 15 shows the result of measurement for the turbidity of the toothpastes containing the amorphous anhydrous silica. In the figures, "C" represents the result just after the preparation of the toothpaste, "D" represents the result after one month storage at a room temperature (about 25° C.) and "E" represents the result after one month storage at 50° C.

TABLE 4

| Formulation | I | II | III | IV |
|---|---|---|---|---|
| Zr-bonded silicate | 20% | 20% | 20% | 20% |
| 96% Glycerin | 19.9 | 20.8 | 21.8 | 22.7 |
| 70% Sorbitol | 39.7 | 41.7 | 43.6 | 45.5 |
| Polyethylene glycol | 5.0 | 5.0 | 5.0 | 5.0 |
| Sodium carboxymethylcellulose | 1.2 | 1.2 | 1.2 | 1.2 |
| Sodium lauryl sulfate | 1.5 | 1.5 | 1.5 | 1.5 |
| Sodium saccharin | 0.1 | 0.1 | 0.1 | 0.1 |
| Flavor | 1.0 | 1.0 | 1.0 | 1.0 |
| Purified water | 11.6 | 8.7 | 5.8 | 3.0 |
| Total | 100.0% | 100.0% | 100.0% | 100.0% |
| Refractive index of toothpaste | 1.445 | 1.450 | 1.455 | 1.460 |

TABLE 5

| Formulation | V | VI | VII | VIII |
|---|---|---|---|---|
| Amorphous anhydrous silica | 20% | 20% | 20% | 20% |
| 96% Glycerin | 19.9 | 20.8 | 21.8 | 22.7 |
| 70% Sorbitol | 39.7 | 41.7 | 43.6 | 45.5 |
| Polyethylene glycol 400 | 5.0 | 5.0 | 5.0 | 5.0 |
| Sodium carboxymethylcellulose | 1.2 | 1.2 | 1.2 | 1.2 |
| Sodium lauryl sulfate | 1.5 | 1.5 | 1.5 | 1.5 |
| Sodium saccharin | 0.1 | 0.1 | 0.1 | 0.1 |
| Flavor | 1.0 | 1.0 | 1.0 | 1.0 |
| Purified water | 11.6 | 8.7 | 5.8 | 3.0 |
| Total | 100.0% | 100.0% | 100.0% | 100.0% |
| Refractive index of toothpaste | 1.445 | 1.450 | 1.455 | 1.460 |

From the results shown in FIG. 14 and FIG. 15, it is recognized that the Zr-bonded silicate, when compared with the usual amorphous anhydrous silica, shows less minimum turbidity and is more suitable than the anhydrous silica as the abrasive for preparing transparent dentifrices. Furthermore, while the Zr-bonded silicate shows less fluctuation in the refractive index even when stored at various temperatures and has excellent aging stability, the anhydrous silica shows significant fluctuation in the refractive index and remarkable aging instability. Specifically, in the transparent dentifrice using an anhydrous silica as the abrasive, the refractive index of the anhydrous silica fluctuates during storage to increase the difference in relation with the refractive index of the transparent vehicle, resulting in a gradual fall of the transparency. On the other hand, in the transparent dentifrice using the Zr-bonded silicate as the abrasive, since the refractive index of the Zr-bonded silicate scarcely fluctuates during storage, the difference of the refractive index in relation with the transparent vehicle scarcely increases, thereby maintaining the transparent appearance.

[EXAMPLE 4]

Toothpastes having the following formulations using the Zr-bonded silicate having a $ZrO_2$ content of 0.5% by weight based on $SiO_2$, the amorphous anhydrous silica and amorphous aluminosilicate as the abrasive, respectively. They were estimated by the Scheffer's paired comparative method with 60 panelers on every item shown in Table 6 according to the following scores. The results are shown in Table 4.

| Toothpaste composition formulation | |
|---|---|
| Abrasive | 10% |
| 96% Glycerin | 22.0 |
| 70% Sorbitol | 43.0 |
| Polyethylene glycol 400 | 5.0 |
| Sodium carboxymethylcellulose | 1.2 |
| Sodium lauryl sulfate | 1.5 |
| Sodium saccharin | 0.1 |
| Flavor | 1.0 |
| Purified water | 6.2 |
| | 100.0% |

Score
+2: very excellent
+1: good
0: identical
−1: poor
−2: extremely poor

TABLE 6

| | Main effect | Average preference | | |
|---|---|---|---|---|
| Item | dispersing rate | Zr-bonded silicate | Amorphous silica | Aluminosilicate |
| Dispersibility | 1.64 | 0.15 | −0.02 | −0.13 |
| Sandy feeling | 5.02** | 0.27 | −0.12 | −0.15 |
| Astringency | 8.27** | 0.22 | −0.28 | −0.07 |
| Overall preference | 1.51 | 0.17 | −0.05 | −0.12 |

Note:
As the result of F test, meaningful 1% difference were recognized for sandy feeling and astringency.

As the results shown in Table 6, it is recognized that the toothpaste using the Zr-bonded silicate provides satisfactory feelings in use.

[EXAMPLE 5]

Transparent toothpastes having the formulations as shown in Table 8 were prepared using the Zr-bonded silicates of the properties shown in Table 7.

TABLE 7

|  | No. 7 | No. 8 | No. 9 | No. 10 |
|---|---|---|---|---|
| $ZrO_2$ content (%) | 0.5 | 0.5 | 0.3 | 2.0 |
| Liquid absorption (ml/g) | 1.06 | 1.23 | 1.20 | 0.81 |
| Refractive index | 1.435 | 1.441 | 1.452 | 1.468 |
| Ignition loss | 8.8 | 9.9 | 7.2 | 5.8 |
| Specific surface area (BET method) (m²/g) | 28 | 42 | 56 | 453 |
| Specific gravity | 2.215 | 2.218 | 2.205 | 2.188 |

TABLE 8

|  |  | IX | X | XI | XII |
|---|---|---|---|---|---|
| Zr-bonded silicate | No. 7 | 10% | — | — | — |
|  | No. 8 | — | 10% | — | — |
|  | No. 9 | — | — | 10% | — |
|  | No. 10 | — | — | — | 10% |
| Gelling amorphous anhydrous silica |  | 3.0 | 2.8 | 2.8 | 3.0 |
| Polyethylene glycol #400 |  | 5.0 | 5.0 | 5.0 | 5.0 |
| 99.5% Glycerin |  | 20.2 | 21.4 | 23.4 | 30.4 |
| 70% Sorbitol |  | 40.4 | 42.6 | 46.8 | 45.6 |
| Sodium carboxymethylcellulose |  | 1.0 | 1.0 | 1.0 | 1.0 |
| Sodium lauryl sulfate |  | 1.5 | 1.5 | 1.5 | 1.5 |
| Sodium saccharin |  | 0.1 | 0.1 | 0.1 | 0.1 |
| Flavor |  | 1.0 | 1.0 | 1.0 | 1.0 |
| Purified water |  | 17.8 | 14.6 | 8.4 | 2.4 |
|  | Total | 100.0% | 100.0% | 100.0% | 100.0% |
| Refractive index |  | 1.438 | 1.442 | 1.452 | 1.462 |
| Turbidity ($T_d/T_t$) |  | 0.11 | 0.08 | 0.08 | 0.10 |

Any of the toothpastes having the foregoing formulation showed excellent transparency. The toothpaste of the formulation IX had RAD value of 66 and showed satisfactory abrasing power.

The Zr-bonded silicates used in the following examples have the properties as shown in Table 9.

TABLE 9

|  | Zr-bonded silicate | | |
|---|---|---|---|
|  | I | II | III |
| $ZrO_2$ content (%) | 0.5 | 0.5 | 2.0 |
| Liquid absorption (ml/g) | 0.93 | 1.05 | 0.81 |
| Refractive index | 1.462 | 1.440 | 1.468 |
| Ignition loss | 5.3 | 9.8 | 5.8 |
| Specific surface area (BET method) (m²/g) | 383 | 20 | 453 |
| Specific gravity | 2.142 | 2.215 | 2.188 |

[EXAMPLE 6]

| Zr-bonded silicate II | 5.0% |
|---|---|
| Gelling amorphous anhydrous silica | 4.0 |
| 96% glycerin | 28.5 |
| 70% sorbitol | 42.7 |
| Polyethylene glycol 400 | 5.0 |
| Sodium carboxymethylcellulose | 1.0 |
| Sodium lauryl sulfate | 1.2 |
| Sodium lauroyl sarcosinate | 0.3 |
| Sodium saccharin | 0.1 |
| Flavor | 1.0 |
| Sodium monofluorophosphate | 0.75 |
| Glycyrrhizinic acid | 0.1 |
| Purified water | balance |
|  | 100.0% |

[EXAMPLE 7]

| Zr-bonded silicate I | 10.0% |
|---|---|
| Gelling amorphous anhydrous silicate | 3.0 |
| 96% glycerin | 20.8 |
| 70% sorbitol | 45.0 |
| Polyethylene glycol 400 | 3.0 |
| Sodium carboxymethylcellulose | 0.9 |
| Sodium lauryl sulfate | 1.2 |
| Sodium lauroyl sarcosinate | 0.5 |
| Sodium saccharin | 0.05 |
| Flavor | 1.1 |
| Chlorohexydine.2HCl | 0.05 |
| ε-aminocaproic acid | 0.1 |
| Purified water | balance |
|  | 100.0% |

[EXAMPLE 8]

| Zr-bonded silicate III | 10.0% |
|---|---|
| Gelling amorphous anhydrous silica | 3.0 |
| 96% glycerin | 28.2 |
| 70% sorbitol | 50.7 |
| Polyethylene glycol 400 | 4.0 |
| Carrageenan | 0.5 |
| Sodium alginate | 0.4 |
| Sodium lauryl sulfate | 1.5 |
| α-olefin sulfonate | 0.3 |
| Sodium saccharin | 0.1 |
| Flavor | 1.0 |
| Chlorohexydine gluconate (20%) | 0.1 |
| Purified water | balance |
|  | 100.0% |

[EXAMPLE 9]

| Zr-bonded silicate I | 15.0% |
|---|---|
| Gelling amorphous anhydrous silica | 2.0 |
| 96% glycerin | 36.0 |
| 70% sorbitol | 36.0 |
| Polyethylene glycol 400 | 4.0 |
| Sodium carboxymethylcellulose | 0.3 |
| Sodium alginate | 0.5 |
| Sodium lauryl sulfate | 1.2 |
| Sucrose monolaurate (average esterification degree: 1.6) | 0.3 |
| Sodium saccharin | 0.1 |
| Flavor | 1.0 |
| Dextranase | 0.2 |
| Purified water | balance |
|  | 100.0% |

[EXAMPLE 10]

| Zr-bonded silicate II | 15.0% |
|---|---|
| Gelling amorphous anhydrous silica | 2.0 |
| 96% glycerin | 32.0 |
| 70% sorbitol | 26.0 |
| Polyethylene glycol 400 | 5.0 |
| Sodium alginate | 0.6 |
| Carbopole/neutralizer | 0.5/0.2 |
| Sodium lauryl sulfate | 1.5 |
| Sodium saccharin | 0.1 |
| Flavor | 1.0 |
| Tranexamic acid | 0.05 |
| Purified water | balance |
|  | 100.0% |

[EXAMPLE 11]

| Zr-bonded silicate III | 20.0% |
|---|---|
| Gelling amorphous anhydrous silica | 1.0 |

-continued

| | |
|---|---|
| 96% glycerin | 23.0 |
| 70% sorbitol | 45.0 |
| Polyethylene glycol 400 | 5.0 |
| Sodium carboxymethylcellulose | 0.6 |
| Xanthane gum | 0.3 |
| Sodium lauroyl sarcosinate | 0.5 |
| α-olefin sulfonate | 1.0 |
| Sodium saccharin | 0.08 |
| Flavor | 1.0 |
| Dihydroxyaluminum allantoin | 0.1 |
| Purified water | balance |
| | 100.0% |

[EXAMPLE 12]

| | |
|---|---|
| Zr-bonded silicate I | 20.0% |
| Gelling amorphous anhydrous silica | 1.0 |
| 96% glycerin | 16.6 |
| 70% sorbitol | 16.8 |
| Polyethylene glycol 400 | 3.0 |
| Carbopole/neutralizer | 0.5/0.2 |
| Xanthane gum | 0.4 |
| α-olefin sulfonate | 1.0 |
| Sucrose monolaurate (average esterification degree: 1.6) | 0.6 |
| Sodium saccharin | 0.1 |
| Flavor | 1.0 |
| Glycyrrhizinic acid | 0.1 |
| Stannous fluoride | 0.41 |
| Purified water | balance |
| | 100.0% |

[EXAMPLE 13]

| | |
|---|---|
| Zr-bonded silicate I | 25.0% |
| Gelling amorphous anhydrous silica | 0.5 |
| 96% glycerin | 36.0 |
| 70% sorbitol | 27.0 |
| Polyethylene glycol 400 | 4.0 |
| Sodium carboxymethylcellulose | 0.2 |
| Sodium alginate | 0.8 |
| Sodium lauryl sulfate | 1.8 |
| Sodium saccharin | 0.12 |
| Flavor | 1.0 |
| Sodium fluoride | 0.22 |
| ε-aminocaproic acid | 0.1 |
| Purified water | balance |
| | 100.0% |

[EXAMPLE 14]

| | |
|---|---|
| Zr-bonded silicate I | 30.0% |
| 96% glycerin | 10.0 |
| 70% sorbitol | 20.0 |
| Polyethylene glycol 400 | 5.0 |
| Carrageenan | 0.1 |
| Sodium alginate | 0.5 |
| α-olefin sulfonate | 1.0 |
| Sucrose monolaurate (average esterification degree: 1.6) | 0.2 |
| Sodium saccharin | 0.12 |
| Flavor | 1.1 |
| ε-aminocaproic acid | 0.1 |
| Purified water | balance |
| | 100.0% |

[EXAMPLE 15]

| | |
|---|---|
| Zr-bonded silicate III | 35.0% |

-continued

| | |
|---|---|
| 96% glycerin | 12.7 |
| 70% sorbitol | 31.5 |
| Polyethylene glycol 400 | 4.0 |
| Sodium carboxymethylcellulose | 0.5 |
| Sodium alginate | 0.1 |
| Sodium lauryl sulfate | 1.0 |
| Sucrose monolaurate (average esterification degree: 1.6) | 0.5 |
| Sodium saccharin | 0.1 |
| Flavor | 1.1 |
| Hydroxyethane diphosphonate | 1.0 |
| Purified water | balance |
| | 100.0% |

[EXAMPLES 16–18]

Toothpaste compositions having the formulations shown in Table 11 were prepared using Zr-bonded silicates IV, V, VI as shown in Table 10.

TABLE 10

| Property of Zr-bonded silicate | | | |
|---|---|---|---|
| | IV | V | VI |
| $ZrO_2$ content (%) | 0.2 | 0.1 | 0.3 |
| Liquid absorption (ml/g) | 0.82 | 1.03 | 1.02 |
| Refractive index | 1.430 | 1.432 | 1.434 |
| Ignition loss | 5.5 | 5.7 | 5.7 |
| Specific surface area (BET method, $m^2/g$) | 23.7 | 305 | 251 |
| Specific gravity | 2.238 | 2.600 | 2.169 |

TABLE 11

| | Example 11 | Example 12 | Example 13 |
|---|---|---|---|
| Zr-bonded silicate IV | 23.0% | — | — |
| Zr-bonded silicate V | — | 30.0% | — |
| Zr-bonded silicate VI | — | — | 33.0% |
| Gelling amorphous anhydrous silica | 0.5 | — | — |
| 99.5% glycerin | 23.6 | 14.9 | 16.7 |
| 70% sorbitol | 23.7 | 29.8 | 25.1 |
| Polyethylene glycol 400 | 4.0 | 5.0 | 4.0 |
| Sodium carboxymethylcellulose | 0.2 | — | 0.5 |
| Carrageenan | — | 0.1 | — |
| Sodium alginate | 0.8 | 0.5 | 0.1 |
| Sodium lauryl sulfate | 1.8 | — | 1.0 |
| α-olefin ($C_{14}$) sulfonate | — | 1.5 | — |
| Sucrose monolaurate (esterification degree: 1.6) | — | 0.2 | 0.5 |
| Sodium saccharin | 0.12 | 0.12 | 0.1 |
| Flavor | 1.0 | 1.0 | 1.1 |
| Sodium fluoride | 0.22 | — | — |
| Tranexamic acid | 0.1 | 0.1 | — |
| Chlorohexydine HCl | — | — | 0.5 |
| Water | balance | balance | balance |
| | 100.0% | 100.0% | 100.0% |

What is claimed is:

1. A dentifrice composition comprising: 1 to 50% by weight of a zirconium-bonded synthetic amorphous silicate (zirconosilicate) with a zirconium content of 0.1 to 10% by weight as $ZrO_2$ based on $SiO_2$ as an abrasive, and a dentifrice vehicle containing an effective stabilizing amount of water and a humectant and an effective flavoring amount of a flavoring material.

2. The dentifrice composition as defined in claim 1, in which the zirconium content of the silicate is in the range of 0.2 to 2% by weight as $ZrO_2$ based on $SiO_2$.

3. The dentifrice composition as defined in claim 1, which is made transparent by adjusting the refractive index of the zirconium-bonded synthetic amorphous silicate and that of the dentifrice vehicle substantially identical to each other.

4. The dentifrice composition as defined in claim 1, in which the zirconium-bonded synthetic amorphous silicate has a refractive index of 1.40 to 1.47, a specific surface area of less than 800 m$^2$/g, a specific gravity of 1.9 to 2.3, and a liquid absorption of 0.4 to 2.0 ml/g.

5. The dentifrice composition as defined in claim 2, which is made transparent by adjusting the refractive index of the zirconium-bonded synthetic amorphous silicate and that of the dentifrice vehicle substantially identical to each other.

6. The dentifrice composition as defined in claim 2, in which the blended amount of the zirconium-bonded synthetic amorphous silicate is in the range of 1 to 50% by weight of the composition.

7. The dentifrice composition as defined in claim 2, in which the zirconium-bonded synthetic amorphous silicate has a refractive index of 1.40 to 1.47, a specific surface area of less than 800 m$^2$/g, a specific gravity of 1.9 to 2.3, and a liquid absorption of 0.4 to 2.0 ml/g.

8. The dentifrice composition as defined in claim 1, in which the zirconium-bonded amorphous silicate has a specific gravity of 1.9 to 2.3.

9. A dentifrice composition, comprising: 1 to 50% by weight based on the weight of the dentifrice composition of an abrasive which is a zirconium-bonded synthetic amorphous silicate (zirconosilicate) with a zirconium content of 0.1 to 10% weight as ZrO$_2$ based on SiO$_2$ and a SiO$_2$ content of more than 70% by weight of the anhydrous matter wherein impurities selected from the group consisting of aluminum, magnesium, sodium, potassium, lithium and hafnium are present in an amount that does not exceed 10% by weight of the silicate; and a dentifrice vehicle containing an effective stabilizing amount of water and a humectant and an effective flavoring amount of a flavoring material.

10. The dentifrice composition as defined in claim 9, in which the zirconium content of the silicate is in the range of 0.2 to 2% by weight as ZrO$_2$ based on SiO$_2$.

11. The dentifrice composition as defined in claim 9, which is transparent.

12. The dentifrice composition as defined in claim 9, which is opaque.

13. The dentifrice composition as defined in claim 9, wherein the zirconosilicate is present in an amount of 5 to 30% by weight based on the total weight of the composition.

14. The dentifrice composition as defined in claim 9, in which the zirconium-bonded synthetic amorphous silicate has a refractive index of 1.40 to 1.47, a specific surface area of less than 800 m$^2$/g, a specific gravity of 1.9 to 2.3, and a liquid absorption of 0.4 to 2.0 ml/g.

15. The dentifrice composition as defined in claim 9, wherein the zirconosilicate is prepared by the reaction of a mineral acid containing a zirconium salt with an alkali metal salt of silicic acid, said zirconium salt being present in an amount sufficient to form a zirconosilicate having 0.1 to 10% by weight as ZrO$_2$ based on SiO$_2$.

16. The dentifrice composition as defined in claim 1, wherein the SiO$_2$ content in said zirconium-bonded synthetic amorphous silicate is more than 70% by weight based on the weight of said zirconium-bonded silicate after being dried at 105° C. for 2 hours.

17. The dentifrice composition as defined in claim 1, wherein the SiO$_2$ content in said zirconium-bonded synthetic amorphous silicate is more than 85% by weight based on the weight of said zirconium-bonded silicate after being dried at 105° C. for 2 hours.

18. The dentifrice composition as defined in claim 1, wherein the flavor is present in an amount of 0.1 to 5% by weight of the composition.

19. The dentifrice composition as defined in claim 1, wherein the flavor is present in an amount of 0.5 to 2% by weight of the composition.

20. The dentifrice composition as defined in claim 1, wherein said zirconium-bonded synthetic amorphous silicate is present in an amount of 5 to 30% by weight of the composition.

21. The dentifrice composition as defined in claim 1, wherein the zirconium content is 0.2 to 2% by weight as ZrO$_2$ based on SiO$_2$.

22. The dentifrice composition as defined in claim 1, wherein said humectant is present in an amount of 10 to 80% by weight of the composition.

23. The dentifrice composition as defined in claim 1, wherein said humectant is present in an amount of 30 to 60% by weight of the composition.

* * * * *